United States Patent
Riedel

(10) Patent No.: US 9,907,333 B2
(45) Date of Patent: Mar. 6, 2018

(54) METHOD AND DEVICE FOR MEASURING THE QUALITY OF CONNECTION IN TOBACCO INDUSTRY'S ARTICLES

(71) Applicant: International Tobacco Machinery Poland Sp. z o. o., Radom (PL)

(72) Inventor: Michael Riedel, Geldern (DE)

(73) Assignee: International Tobacco Machinery Poland Sp. z o. o., Radom (PL)

( * ) Notice: Subject to any disclaimer, the term of this patent is extended or adjusted under 35 U.S.C. 154(b) by 172 days.

(21) Appl. No.: 14/887,081

(22) Filed: Oct. 19, 2015

(65) Prior Publication Data
US 2016/0113322 A1    Apr. 28, 2016

(30) Foreign Application Priority Data
Oct. 28, 2014  (PL) .......................................... 409885

(51) Int. Cl.
*A24C 5/34*     (2006.01)
*A24C 5/343*    (2006.01)
(Continued)

(52) U.S. Cl.
CPC ................ *A24C 5/343* (2013.01); *A24C 5/34* (2013.01); *G01N 19/04* (2013.01); *A24C 1/30* (2013.01); *A24C 1/44* (2013.01); *A24C 5/39* (2013.01)

(58) Field of Classification Search
CPC .... A24C 1/10; A24C 1/12; A24C 1/14; A24C 1/26; A24C 1/28; A24C 1/30; A24C 1/44;
(Continued)

(56) References Cited

U.S. PATENT DOCUMENTS 4,484,591 A * 11/1984 Wahle ...................... A24C 5/34
                                                        131/280
4,721,119 A *  1/1988 Ludszeweit .............. A24C 5/24
                                                        131/67
(Continued)

FOREIGN PATENT DOCUMENTS

CN      102809533      12/2012
GB       1077058       7/1967
(Continued)

OTHER PUBLICATIONS

European Search Report for application EP 15 18 9591 dated Mar. 14, 2016.
(Continued)

*Primary Examiner* — Randy Gibson
*Assistant Examiner* — Gedeon M Kidanu
(74) *Attorney, Agent, or Firm* — Oppedahl Patent Law Firm LLC

(57) ABSTRACT

The object of the application is a method for measuring the quality of connection in a tobacco industry's rod-like article comprising a rod (1A, 1B) with a filler (2, 3, 5, 6) and a wrapper (4A, 4B), characterized in that the tested rod (1A, 1B) used in the tobacco industry's article is fixed in a measuring device in a seat (11) for fixing the rod (1A, 1B) in a rotary measuring table (10), then the rotary measuring table (10) is put in rotary motion, by means of the measuring unit the advancement of the filler (3, 6) of the tested rod from the wrapper (4A, 4B) is measured, and the quality of connection between the wrapper (4A, 4B) and the rod (1A, 1B) filler (3, 6) is determined on the basis of the extent of advancement of the rod (1A, 1B) filler (3, 6), and the centrifugal force. The object of the application is also a device for measuring the quality of connection.

8 Claims, 5 Drawing Sheets

(51) Int. Cl.
*G01N 19/04* (2006.01)
*A24C 5/39* (2006.01)
*A24C 1/30* (2006.01)
*A24C 1/44* (2006.01)

(58) Field of Classification Search
CPC .. A24C 3/00; A24C 5/34; A24C 5/343; A24C 5/02; A24C 5/04; A24C 5/14; A24C 5/08; A24C 5/10; A24C 5/18; A24C 5/39; A24B 11/00; G01N 19/04
USPC ..... 73/150 A, 760, 788, 826, 835, 841, 843, 73/845, 855, 856, 856.9, 865.3; 131/906
See application file for complete search history.

(56) References Cited

U.S. PATENT DOCUMENTS

| | | | | |
|---|---|---|---|---|
| 5,144,845 A | * | 9/1992 | Pyke | G01N 19/04 73/150 A |
| 5,232,100 A | * | 8/1993 | Lewis | B07C 5/065 209/537 |
| 5,594,184 A | * | 1/1997 | Schroder | A24C 5/3424 177/1 |
| 7,707,895 B2 | * | 5/2010 | Beck | G01N 19/04 73/827 |
| 8,662,088 B2 | | 3/2014 | Owczarek | |
| 8,677,813 B2 | * | 3/2014 | Sellars | G01N 19/04 73/150 A |
| 8,869,969 B2 | | 10/2014 | Cie likowski et al. | |
| 8,925,708 B2 | | 1/2015 | Cie likowski et al. | |
| 8,967,370 B2 | | 3/2015 | Cieslikowski | |
| 9,004,261 B2 | | 4/2015 | Cie likowski et al. | |
| 9,061,835 B2 | | 6/2015 | Gielniewski | |
| 9,161,571 B2 | | 10/2015 | Sikora | |
| 2004/0226465 A1 | * | 11/2004 | Morke | A24C 5/472 101/483 |
| 2008/0302190 A1 | * | 12/2008 | Beck | G01N 19/04 73/827 |
| 2013/0087056 A1 | | 4/2013 | Chojnacki | |
| 2014/0011652 A1 | | 1/2014 | Cieslikowski et al. | |
| 2014/0097107 A1 | | 4/2014 | Zagajska | |
| 2014/0123826 A1 | | 5/2014 | Cieslikowski et al. | |
| 2014/0158252 A1 | | 6/2014 | Owczarek | |
| 2014/0235416 A1 | | 8/2014 | Lisowski et al. | |
| 2014/0371047 A1 | * | 12/2014 | Lerche | G01N 1/00 494/10 |
| 2015/0013519 A1 | | 1/2015 | Cieslikowski et al. | |
| 2015/0047137 A1 | | 2/2015 | Gielniewski | |
| 2015/0068376 A1 | | 3/2015 | Boleslawski | |
| 2015/0114543 A1 | | 4/2015 | Riedel | |
| 2015/0114988 A1 | | 4/2015 | Riedel | |
| 2015/0342247 A1 | | 12/2015 | Ugrewicz | |
| 2016/0000142 A1 | | 1/2016 | Stanikowski et al. | |

FOREIGN PATENT DOCUMENTS

| | | |
|---|---|---|
| GB | 1086935 | 10/1967 |
| WO | 2006/050996 A1 | 5/2006 |
| WO | 2011/114439 A1 | 9/2011 |

OTHER PUBLICATIONS

Polish Search Report for application P.409885 dated Jun. 22, 2015.
English translation of Polish Search Report for application P.409885 dated Jun. 22, 2015.
Search report dated Jun. 22, 2015 for Polish Patent Application P.409885.

* cited by examiner

METHOD AND DEVICE FOR MEASURING THE QUALITY OF CONNECTION IN TOBACCO INDUSTRY'S ARTICLES

BACKGROUND

The object of the invention is a method and a device for measuring the quality of connection in tobacco industry's articles.

The invention is used in the tobacco industry, in particular to measure the quality of adhesive connection between the wrapper and the filler of a rod used in the tobacco industry.

At present, both filter made of a single filter material and of multiple different materials, so-called multi-segment filters, are used. Rods containing a single kind of filter material are formed by cutting a continuous filter rod which is formed by wrapping a filter fibre strand with a wrapper. In the subsequent production process, the rods are cut into a plurality of individual filters applied to cigarettes. Multi-segment rods are formed by cutting a continuous rod which is formed by wrapping multiple segments of different filter materials. In both cases, a rotary cutting head with knives situated on its circumference is used. In case of multi-segment rods, the cutting of the rods usually consists in cutting one of the segments into halves. In the subsequent production process, multi-segment rods are cut into a plurality of individual filters applied to cigarettes. In a finished cigarette, the first segment is adapted to be held by the smoker in the mouth. It is commonly expected that during smoking this segment does not fall out of a cigarette or fall into the smoker's mouth. With regard to filters made of a single material it is also expected that it will not move relative to the wrapper. A commonly used method of segment fixing is to glue them to the wrapper. At present, the cigarette manufacturers use various filter materials as well as various filter wrapper materials. From the viewpoint of adhesive bonding of filter materials and wrapper materials, a very significant issue is the spread of the adhesive in the space between the surfaces to be glued, and the penetration of the adhesive into the structures of both the wrapper and the filter material. These are the factors determining the force holding the segments in the wrapper, i.e. the force of connection of the segments with the wrapper. One or more glue paths are used to fix the segments, whereas such paths may have different shapes. Among the manufacturers of tobacco industry products there is a demand for a device checking the quality of connection of the segments with the wrapper in particular of short segments placed at the end of the filter tip for which the surface to be glued with the wrapper is small. Moreover, there is a demand for a device checking the tobacco filler's holding force in cigarettes depending on the elasticity of tobacco, the filling degree and the friction forces between the tobacco fibres and the wrapper material.

The U.S. Pat. No. 5,144,845 document disclosed a device designed to check the adhesive connection, comprising a movable carriage on which one of the tested materials may be fixed and an anvil in which the second of tested materials may be mounted. The device also comprises means for the application of glue in order to form a glue layer between tested materials. These means are mounted on a movable carriage. Moreover, the device comprises carriage moving means, and means designed to push the carriage and the anvil which, together, connect both materials with each other with the layer of applied glue placed between them. Then, an attempt to separate the tested materials by pushing the carriage and the anvil apart is made and the force needed to separate them is measured by means of a strain gauge.

SUMMARY OF THE INVENTION

The objective of this invention is to develop a method and a device which will allow testing the quality of connection of tobacco industry's articles, in particular multi-segment rods, without introducing stresses to tested articles and without deforming them.

The substance of the invention is a method for measuring the quality of connection in a tobacco industry's rod-like article containing a rod with the filler, and a wrapper. According to the invention, the tested rod used in the tobacco industry's article is fixed in the measuring device in a rod fixing seat in a rotating measuring table, then the measuring table is put in rotary motion, by means of the measuring unit the advancement of the filler of tested rod from the wrapper is measured, and the quality of connection between the wrapper and the rod filler is determined on the basis of the extent to which the rod filler has advanced from the wrapper, and the centrifugal force.

A method according to the invention is characterised in that the quality of the tested rod is determined on the basis of the centrifugal force measured indirectly by taking the rotational speed and the physical parameters of the rotary table and the tested product into consideration, or directly by means of a centrifugal force sensor.

A method according to the invention is characterised in that the rotary measuring table is put in rotary motion, after which the rotational speed of the measuring table is set at a constant level and maintained at the set level over a certain period of time.

A method according to the invention is characterised in that the rotary measuring table is put in rotary motion, whereas the rotary motion of the measuring table increases in time.

A method according to the invention is characterised in that the test is interrupted when the advancement of the rod filler has exceeded a certain limit or a certain period of time has elapsed.

The substance of the invention is also a device for measuring the quality of connection in a tobacco industry's rod-like article containing a rod with the filler, and a wrapper. According to the invention, the device comprises a power-driven rotary measuring table with adjustable rotational speed, seats for fixing rods used in tobacco industry's articles disposed in the rotary measuring table, a measuring unit comprising a sensor measuring the extent of advancement of the rod filler from the wrapper, and a control unit designed to determine the quality of connection between the wrapper and the rod filler on the basis of the extent of advancement of the rod filler, and the centrifugal force.

A device according to the invention is characterised in that the rod fixing seats are designed radially in the rotary measuring table.

A device according to the invention is characterised in that the rod fixing seats are designed in the rotary measuring table at an angle to the radius, and the control unit is designed to determine the quality of connection between the wrapper and the filler of a rod used in the tobacco industry, also on the basis of the angle between the rod fixing seat and the radius of the rotary measuring table.

A device according to the invention is characterised in that the measuring unit sensor is selected from a group comprising: mechanical sensors, optical sensors, electromagnetic sensors.

A device according to the invention is characterised by comprising a centrifugal force sensor.

Due to the use of a method and a device according to the invention, a high accuracy of measurement of the article filler holding force may be achieved. Moreover, it is not necessary to affect the filler of the tested article, it is not deformed, and no elements are fixed or glued to it. As a result, the measurement conditions are repeatable.

BRIEF DESCRIPTION OF THE DRAWINGS

The object of the invention was shown in detail in a preferred embodiment in a drawing in which.

DETAILED DESCRIPTION

Figure 1:
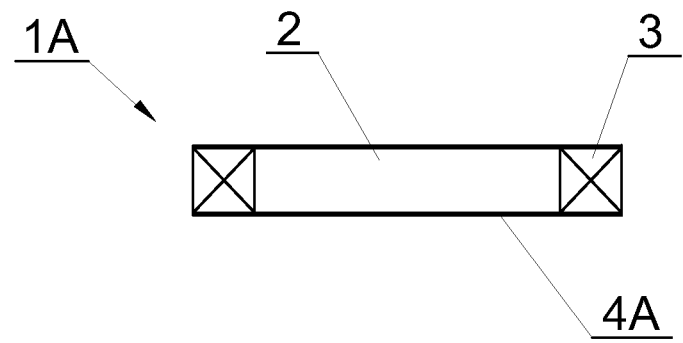
FIG. 1 shows an example of a multi-segment rod.
Figure 2:
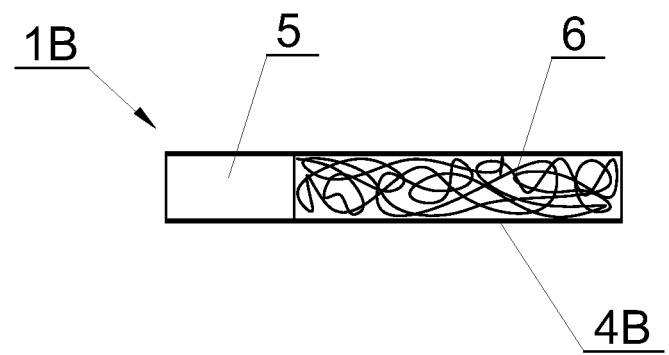
FIG. 2 shows another example of a multi-segment rod in the form of a filter cigarette.

This invention concerns any products and semi-finished products of the tobacco industry, including multi-segment filter rods comprising filter segments, multi-segment filter rods comprising filter segments and additional components changing the article's aroma or giving such aroma, multi-segment filter rods comprising filter segments and additional objects changing the filter properties of filter materials used, multi-segment rods comprising both filter and non-filter segments, multi-segment articles with a reduced tobacco content as well as cigarettes with a single-segment or multi-segment filter tip stuck on. All elements and materials contained in the rods will be hereinafter referred to as the segments or the filler. The segments are wrapped with a joint wrapper, forming a rod being a tobacco industry's article. The tobacco industry's article may comprise connected rods wrapped with a wrapper which connects individual rods. FIGS. 1 and 2 show examples of the tobacco industry's rods 1A and 1B. The multi-segment filter rod 1A comprises the segment 2 of one kind and two segments 3 of another kind wrapped with the wrapper 4A. In practice, also the rods with a greater number of segments can be found and usually all segments are glued to the wrapper. The rod 1B being a filter cigarette comprises a filter portion 5 constituting the tip and a tobacco portion 6 wrapped with the tipping 4B.

Figure 3:
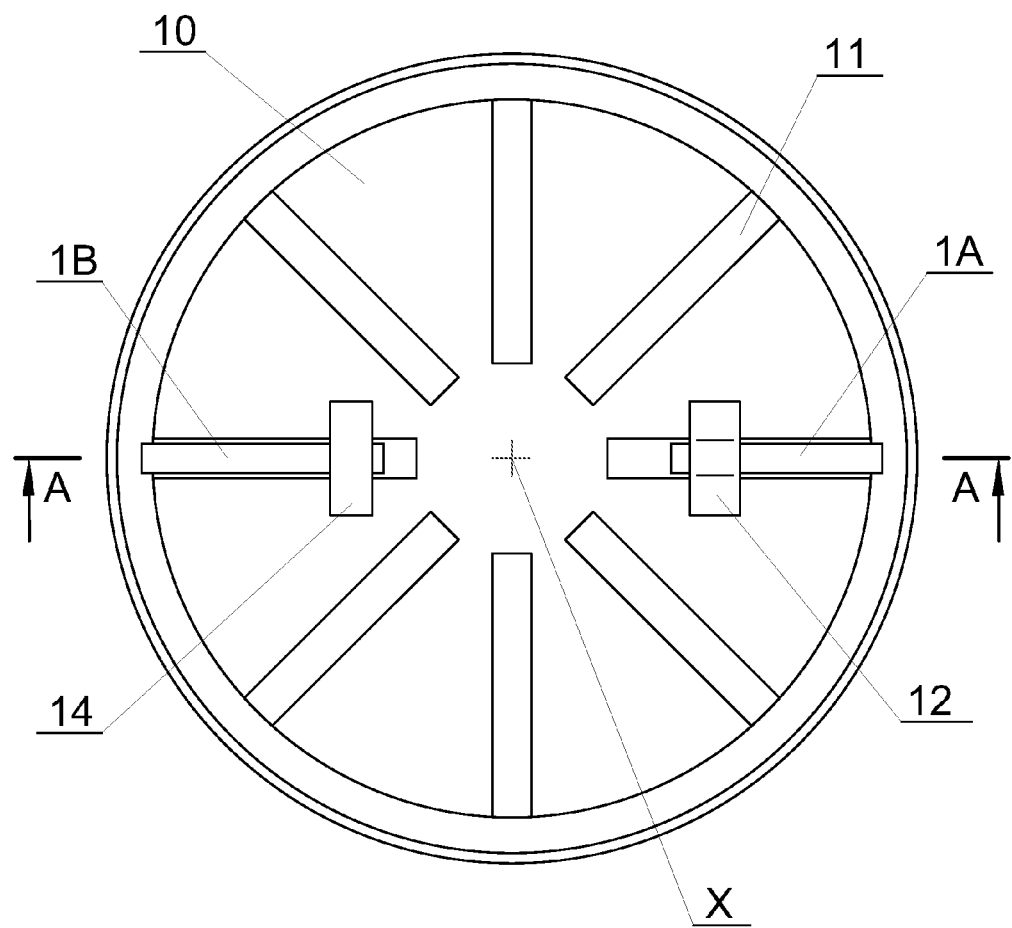
FIG. 3 shows a top view of a rotary measuring table.
Figure 4:
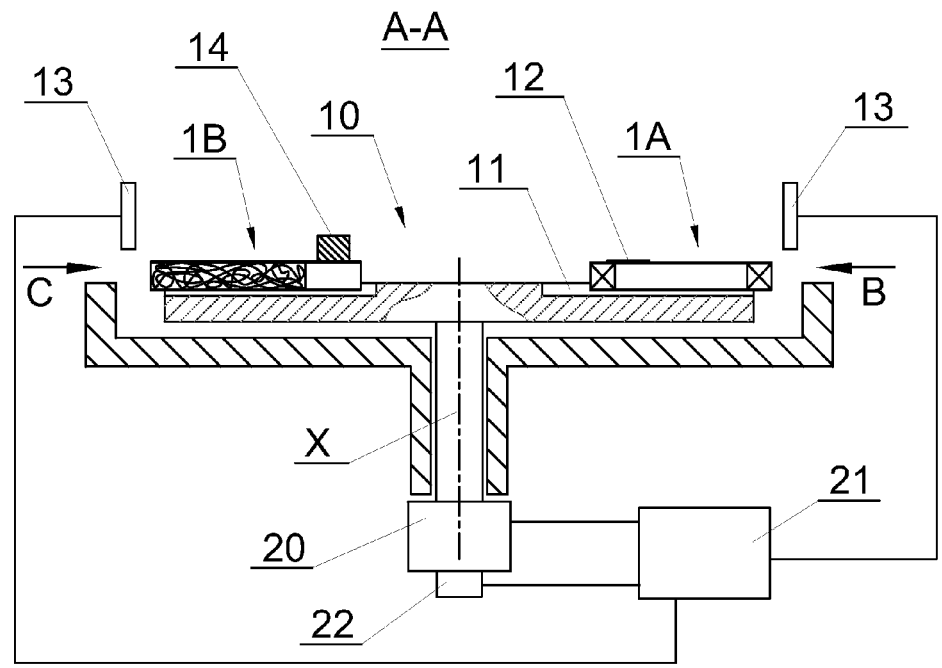
FIG. 4 shows the rotary measuring table of FIG. 2 in a cross-section before the commencement of the test.
Figure 5:
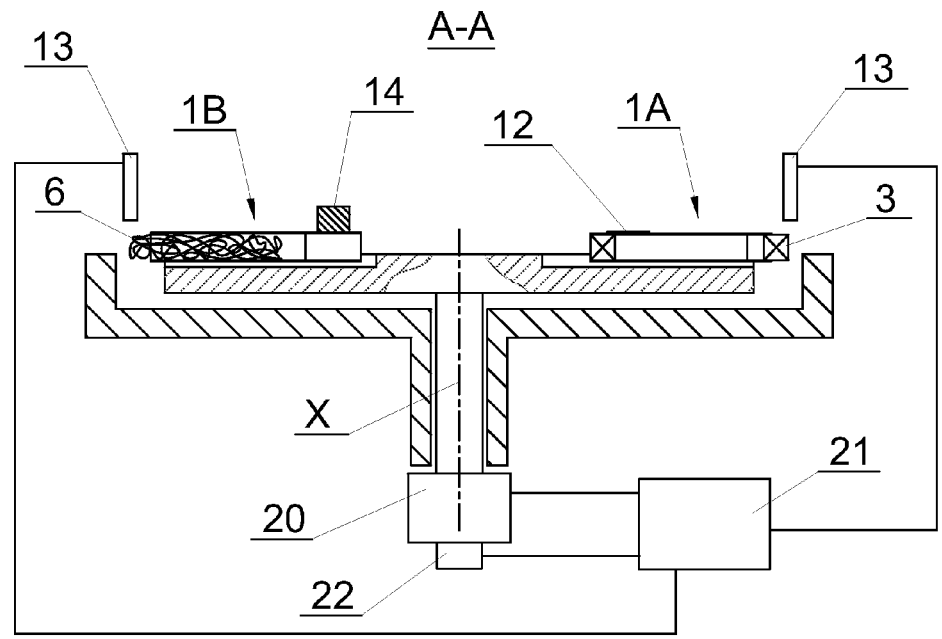
FIG. 5 shows the rotary measuring table of FIG. 2 in a cross-section after the test.
Figure 6:
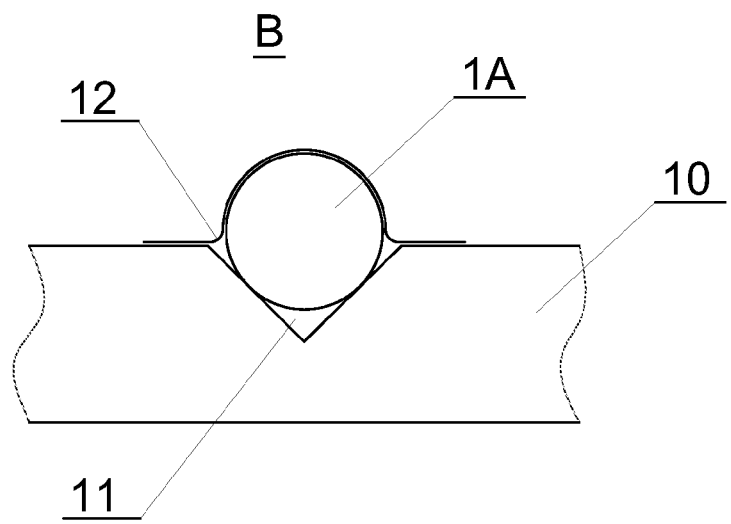
FIG. 6 shows a view of the rod of FIG. 4 fixed by means of an adhesive tape.
Figure 7:
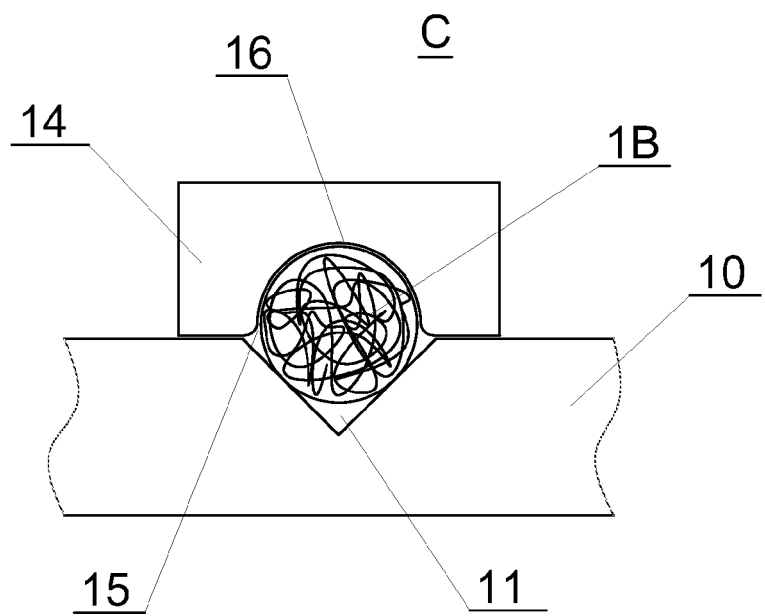
FIG. 7 shows a view of the rod of FIG. 4 fixed by means of a holder.
Figure 8:
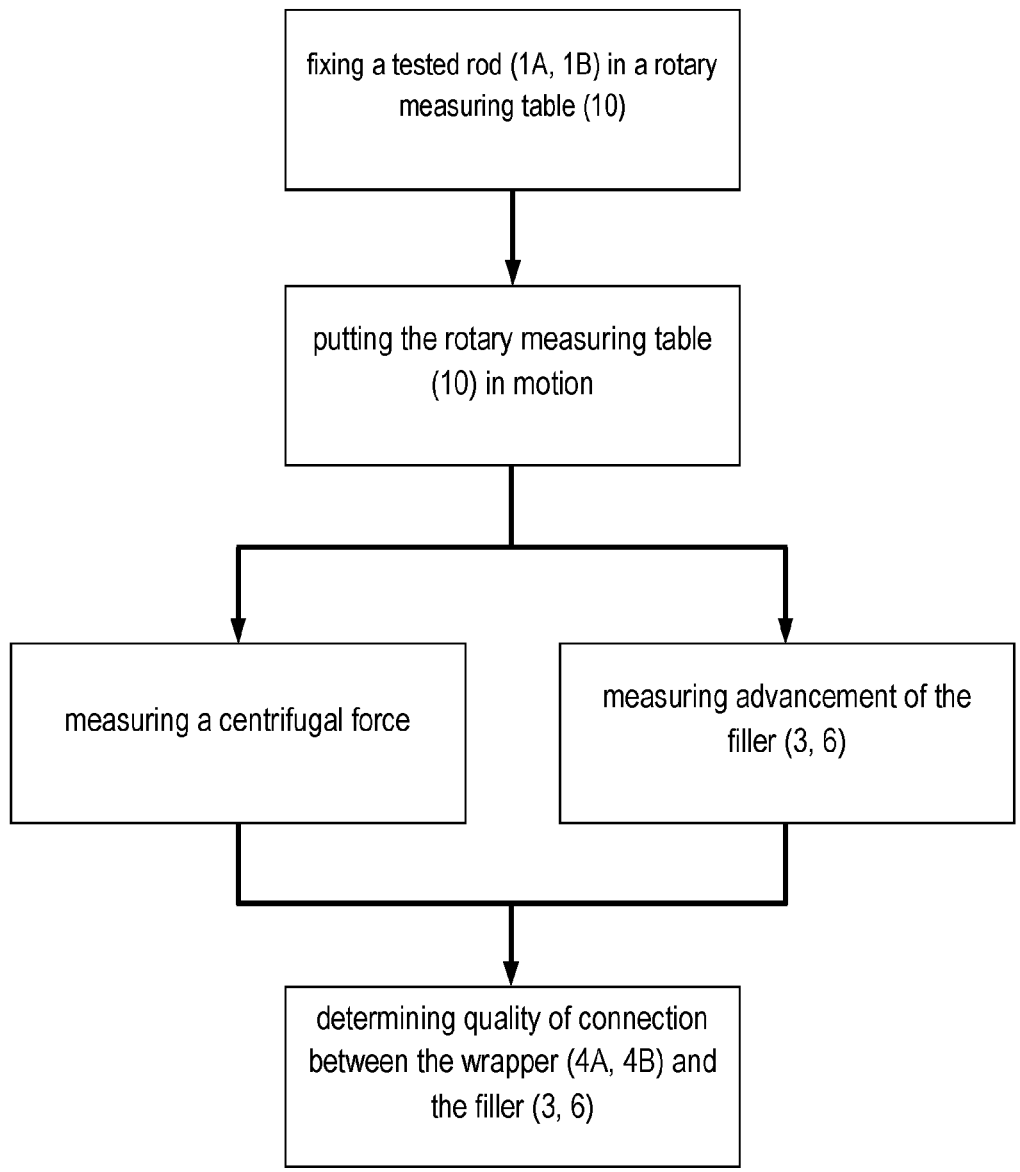
FIG. 8 shows an example of a method of the measurement of the quality of connection between the wrapper and filler.

The measuring table 10 with the axis of rotation X, shown in a top view in FIG. 3 and in a cross-section A-A in FIG. 4, is provided with seats 11 designed for example in the form of longitudinal depressions 1A, 1B, adapted to receive the rods 1A, 1B, whereas the seats 11 may be for example cylindrical, adapted to the rod diameter, or may have flat surfaces inclined relative to one another. The seats 11 may be designed radially or at a certain angle to the radial direction. The filter rod 1A shown in FIG. 3 is stuck by means of an adhesive tape 12, which was also shown in the view B in FIG. 6. FIG. 3 also shows another rod 1B, which is fixed by means of a holder 14 which can be screwed to the measuring table or fastened in another way. The rod 1B is also shown in the view C in FIG. 7. The holder 14 has, in the depression 15 on the side of the rod 1B, a rough holding surface 16, for example with the texture of abrasive paper, or such surface is provided with needles (not shown) which hold the wrapper 4B. The needles on the holding surface 16 may stick in the wrapper 4B only; they may also penetrate into the tip 5, which will not affect the measurement of the holding force of the tobacco portion 6.

A rod to be tested is placed in the seat 11 on the rotary measuring table 10, and then fixed using the fixing means 12, 14. The device comprises a measuring unit including among others a control unit, a rotational speed sensor and advancement sensors. The rotary table 10 is put in rotary motion by means of a drive 20, whereas the rotational speed is given by the control unit 21 and controlled by means of the rotational speed sensor 22. During the rotary motion, a centrifugal force acts on the rod filler, whereas the centrifugal force will grow with increasing rotational speed. The centrifugal force is counterbalanced by a force provided by the connection between the filler and the wrapper. Once the maximum force which can be provided by the connection has been achieved or exceeded, the filler 3, 6 will advance, which will be detected by the sensor 13, and the signal informing that the filler has advanced will be sent to the control unit 21. If a certain limit of advancement is exceeded the measuring table is stopped. For each advancement of the filler, a rotational speed at which the advancement occurred will be recorded, which with the knowledge of physical parameters such as geometrical parameters and the mass of the filler will make it possible to calculate the force of connection of the filler with the wrapper.

It may happen that the advancing of the filler will occur gradually, or the filler will become deformed and it will be difficult to explicitly determine the moment at which the filler has advanced. In such case, it is possible to use several sensors whose task will be to measure the extent of advancement with increasing rotational speed of the measuring table. It is possible to simultaneously make measurements for a plurality of test pieces. The test may also be performed in such a way that the tested rods are placed on the rotary table, after putting the measuring table in rotary motion the rotational speed is increased to a certain value and such speed is maintained for a certain time and then, after stopping the device, an assessment of the connection of the filler with the wrapper is made. When testing a number of rods of one kind the tests may be automated, where the criterion of quality control is any advancement of the filler or not exceeding a certain value of advancement then the visual assessment of the tested rod will not be necessary. However, in case of the need of a detailed analysis of behaviour of the rod filler during the test a visual assessment will always be necessary.

The invention claimed is:

1. A method of measuring quality of connection in a tobacco industry's rod-like article comprising a rod (1A, 1B) with a filler (2, 3, 5, 6) and a wrapper (4A, 4B), comprising the steps of:

fixing a tested rod (1A, 1B) used in the tobacco industry's rod-like article in a seat (11) for fixing the rod (1A, 1B) in a rotary measuring table (10) in a measuring device, putting the rotary measuring table (10) in rotary motion, measuring a centrifugal force and an advancement of the filler (3, 6) of the tested rod from the wrapper (4A, 4B) by means of a measuring unit, and determining quality of connection between the wrapper (4A, 4B) and the filler (3, 6) of the rod (1A, 1B) on the basis of an extent of advancement of the rod (1A, 1B)

filler (3, 6), and a centrifugal force, wherein the centrifugal force is measured indirectly by taking rotational speed of the rotary table (10) and physical parameters of the tested product into consideration, wherein putting the rotary measuring table (10) in rotary motion further comprises increasing rotational speed of the measuring table (10) over time or setting a rotational speed of the measuring table (10) at a constant level and maintaining at the set level over a predefined period of time, and wherein the measurement of the advancement of the filler (3, 6) of the tested rod further comprises interrupting the measurement when the advancement of the rod (1A, 1B) filler has exceeded a predefined limit or a predefined period of time has elapsed.

2. The method of claim 1, wherein the measurement of the advancement of the filler (3, 6) of the tested rod further comprises interrupting the measurement when the advancement of the rod (1A, 1B) filler has exceeded the predefined limit or the predefined period of time has elapsed.

3. The method of claim 1, wherein putting the rotary measuring table (10) in rotary motion further comprises setting the rotational speed of the measuring table (10) at a constant level and maintaining at the set level over the predefined period of time.

4. The method of claim 3, wherein the measurement of the advancement of the filler (3, 6) of the tested rod further comprises interrupting the measurement when the advancement of the rod (1A, 1B) filler has exceeded the predefined limit or the predefined period of time has elapsed.

5. A device for measuring quality of connection in a tobacco industry's rod-like article comprising a rod (1A, 1B) with a filler (2, 3, 5, 6) and a wrapper, comprising:

a power-driven rotary measuring table (10) with adjustable rotational speed, seats (11) for fixing rods used in tobacco industry's articles, situated in the rotary measuring table (10), a measuring unit comprising
a sensor (13) for measuring an extent of advancement of the rod filler (3, 6) from the wrapper (4A, 4B),
and a control unit (21) adapted to determine a quality of connection between the wrapper (4A, 4B) and the rod (1A, 1B) filler (3, 6) on the basis of the extent of advancement of the rod (1A, 1B) filler (3, 6), and a centrifugal force.

6. The device of claim 5 wherein the seats (11) for rod (1A, 1B) fixing are positioned radially in the rotary measuring table (10).

7. The device of claim 5 characterised in that the sensor (13) of the measuring unit is selected from a group comprising: mechanical sensors, optical sensor, electromagnetic sensors.

8. The apparatus of claim 5 wherein the centrifugal force is measured indirectly by taking rotational speed of the rotary table (10) and physical parameters of the tested product into consideration, wherein putting the rotary measuring table (10) in rotary motion further comprises increasing rotational speed of the measuring table (10) over time or setting a rotational speed of the measuring table (10) at a constant level and maintaining at the set level over a predefined period of time, and wherein the measurement of the advancement of the filler (3, 6) of the tested rod further comprises interrupting the measurement when the advancement of the rod (1A, 1B) filler has exceeded a predefined limit or a predefined period of time has elapsed.

* * * * *